(12) United States Patent
Kodak

(10) Patent No.: US 10,898,602 B2
(45) Date of Patent: Jan. 26, 2021

(54) ALCOHOL VAPOR DEODORIZATION SYSTEM

(71) Applicant: James Allen Kodak, Odenton, MD (US)

(72) Inventor: James Allen Kodak, Odenton, MD (US)

( * ) Notice: Subject to any disclaimer, the term of this patent is extended or adjusted under 35 U.S.C. 154(b) by 136 days.

(21) Appl. No.: 16/261,429

(22) Filed: Jan. 29, 2019

(65) Prior Publication Data

US 2020/0237942 A1 Jul. 30, 2020

(51) Int. Cl.
*A61L 2/18* (2006.01)
*D06B 9/00* (2006.01)
*D06B 1/04* (2006.01)

(52) U.S. Cl.
CPC ............... *A61L 2/18* (2013.01); *D06B 1/04* (2013.01); *D06B 9/00* (2013.01); *A61L 2202/26* (2013.01); *D06B 2700/18* (2013.01)

(58) Field of Classification Search
CPC ..................................................... C11D 3/386
USPC ............ 422/28, 33, 292, 295, 298; 510/382; 252/8.86; 8/490
See application file for complete search history.

(56) References Cited

U.S. PATENT DOCUMENTS

| | | | | |
|---|---|---|---|---|
| 5,238,587 A * | 8/1993 | Smith | ............. | C11D 1/825 510/277 |
| 5,658,651 A * | 8/1997 | Smith | ............. | C11D 3/001 442/102 |
| 5,789,368 A * | 8/1998 | You | ............. | D06F 43/00 383/117 |
| 6,663,830 B1 * | 12/2003 | Tindall | ............. | A01N 31/02 422/28 |
| 6,753,306 B2 * | 6/2004 | Simpson | ............. | A01N 61/00 134/25.2 |
| 6,759,006 B1 * | 7/2004 | Siklosi | ............. | A61L 2/07 422/1 |
| 7,008,600 B2 * | 3/2006 | Katsigras | ............. | A01N 59/00 422/1 |
| 7,807,118 B2 * | 10/2010 | Green | ............. | A61L 2/22 422/292 |
| 7,947,086 B2 * | 5/2011 | Panandiker | ............. | C11D 17/049 8/137 |
| 8,008,247 B2 * | 8/2011 | Falk | ............. | D06L 4/27 510/519 |
| 8,563,017 B2 * | 10/2013 | Cunningham | ............. | A01N 37/16 424/405 |
| 8,642,054 B2 * | 2/2014 | Green | ............. | A61F 13/00017 424/401 |

(Continued)

FOREIGN PATENT DOCUMENTS

| | | | | |
|---|---|---|---|---|
| JP | 2004-33729 A | * | 5/2003 | ............. A61L 9/01 |
| JP | 2004-337219 | * | 5/2003 | ............. A61L 9/01 |

OTHER PUBLICATIONS

English Translation JP 2004-337219 A (Year: 2003).*
English Translation of JP 2004-337219 (Year: 2003).*

*Primary Examiner* — Nina Bhat

(57) ABSTRACT

A system that deodorizes gear, padding, or other apparel by killing the bacteria that cause odor. Articles to be deodorized are placed within a re-sealable airtight bag along with highly pure anhydrous ethanol. As the ethanol vaporizes, the gaseous ethanol readily dissolves within the aqueous environment that envelops the bacteria. Ethanol levels within this moisture gradually increase and eventually become bactericidal.

3 Claims, 1 Drawing Sheet

(56) References Cited

U.S. PATENT DOCUMENTS

| | | | | |
|---|---|---|---|---|
| 9,481,961 B2 * | 11/2016 | Parekh | ............... | D06M 13/152 |
| 2001/0044399 A1 * | 11/2001 | Keppie | ............... | C11D 17/047 |
| | | | | 510/327 |
| 2001/0053333 A1 * | 12/2001 | Messier | ............... | A01N 59/00 |
| | | | | 422/28 |
| 2006/0228250 A1 * | 10/2006 | Brown | ..................... | A61L 9/14 |
| | | | | 422/5 |
| 2016/0136698 A1 * | 5/2016 | Kaufman | ............... | A47L 25/00 |
| | | | | 134/93 |

* cited by examiner

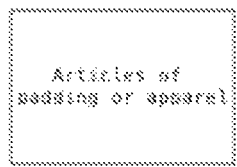 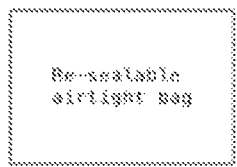 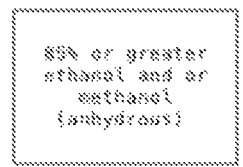
1          2          3

ALCOHOL VAPOR DEODORIZATION SYSTEM

BACKGROUND OF INVENTION

Commercialized efforts at deodorizing padding and apparel without washing usually involve masking unpleasant odors with perfumes that quickly wear off. There is little point in employing bactericidal sprays for deodorization because the liquid can only affect the surface of any article while the vast majority of the bacterial population remains unaffected.

It is therefore necessary to use bactericidal gases in order to kill odors at the source. One very effective way to do this is through the use of ozone. There is a substantial selection of machines on the market today in which the user places the articles to be deodorized in an airtight vessel that produces ozone through electrical discharge. This method can kill odor-causing bacteria in less than 30 minutes. Unfortunately, due to their fundamental bulk and expense, this method is too cumbersome for most consumers. It is preferable to find a generally safe, bactericidal gas that can be deployed quickly and cheaply.

SUMMARY OF INVENTION

Enclosed is a deodorization system for padding and apparel that works by destroying the viability of odor-causing bacteria. This is accomplished by the release of ethanol vapor within the confines of a sealed bag. This vapor gradually dissolves into the aqueous surroundings of the bacteria and eventually reaches levels that stress and then kill the bacteria.

BRIEF DESCRIPTION OF THE DRAWINGS

FIG. 1: shows the alcohol vapor deodorization system.

DETAILED DESCRIPTION OF THE INVENTION

Articles to be deodorized are placed in a re-sealable airtight bag and an anhydrous alcohol mixture that is at least 85% ethanol and/or methanol is poured on top of the articles prior to sealing the bag.

The bag must be sealable to prevent ethanol vapors from escaping. Preferably, this would be accomplished through the use of a zippered bag or simply cinching a thick plastic bag using a releasable cable tie.

As an alternative to pouring the ethanol directly on the articles, the ethanol could be poured into a receptacle resistant to spillage but with sufficient openings to permit the vapor to escape the receptacle and into the bag. However, in the preferred embodiment, the ethanol should be poured directly over the articles. This simple step maximizes the surface area of the liquid ethanol and enables it to reach its equilibrium vapor pressure at a much faster rate than keeping it within a receptacle. This in turn speeds the deodorization process.

With the passage of time, more and more ethanol vapor dissolves into the aqueous environment that surrounds the bacteria living within the articles. As the ethanol levels rise, the bacteria become increasingly stressed and eventually die. The process of deodorization, affected by temperature, moisture levels, and the quantity of ethanol relative to the load, usually takes 12-24 hours.

The most important criteria for a practical, no wash, deodorization system include: (1) an active agent that is stored in a solid or liquid form, (2) possessing a high equilibrium vapor pressure, (3) that readily dissolves into an aqueous environment, (4) that is toxic to bacteria, and (5) can be applied safely by humans. 85% or better anhydrous ethanol maximizes this family of variables more than any other substance.

In general there are many alcohols that readily dissolve in water and can be readily stored in liquid form. However, methanol and ethanol are distinguished in that they both possess equilibrium vapor pressures several times greater than any of the higher molecular weight alcohols. While methanol and ethanol both exhibit considerable anti-microbial properties, ethanol is far less toxic and is thus the preferred active agent for this purpose.

To maximize the rate of evaporation and thereby increase the rate at which ethanol dissolves into the aqueous environment surrounding the odor-causing bacteria, the ethanol should come in an anhydrous form. Furthermore, since anhydrous mixtures of ethanol, such as completely denatured alcohol, contain volatile additives that are themselves hazardous, it is ideal to minimize the additive presence by using highly pure varieties, 85% ethanol or better.

I claim:

1. A process for deodorizing articles of apparel or padding that consists of placing the articles in an airtight bag or other airtight container, adding a disinfecting anhydrous composition that is at least 85% ethanol or at least 85% methanol by volume, or a mixture of the two alcohols in which their combined volumes is at least 85% of the total volume of the mixture, followed by sealing the airtight bag or container.

2. A process for deodorizing articles of apparel or padding that consists of placing the articles in an airtight bag or other airtight container, adding a disinfecting anhydrous composition that is at least 85% ethanol by volume, followed by sealing the airtight bag or container.

3. A process for deodorizing articles of apparel or padding that consists of placing the articles in an airtight bag or other airtight container, adding a disinfecting anhydrous composition that is at least 85% methanol by volume, followed by sealing the airtight bag or container.

* * * * *